United States Patent [19]

Tarzia et al.

[11] 4,010,159
[45] Mar. 1, 1977

[54] PYRROLO[3,4-D]PYRIMIDINES AND METHODS FOR THEIR PREPARATION

[75] Inventors: Giorgio Tarzia, Rome; Gianbattista Panzone, Cornaredo (Milan), both of Italy

[73] Assignee: Gruppo Lepetit S.p.A., Milan, Italy

[22] Filed: Mar. 17, 1975

[21] Appl. No.: 559,192

[30] Foreign Application Priority Data

Mar. 20, 1974 United Kingdom ............ 12369/74

[52] U.S. Cl. .......................... 260/256.4 F; 424/251
[51] Int. Cl.² ...................................... C07D 487/04
[58] Field of Search ............................ 260/256.4 F

[56] References Cited

UNITED STATES PATENTS 3,682,918  8/1972  Druey et al. ................. 260/256.4 F
3,804,835  4/1974  Wiedemann et al. ....... 260/256.4 F Primary Examiner—Donald G. Daus
Assistant Examiner—James H. Turnipseed
Attorney, Agent, or Firm—Theodore Post; C. Kenneth Bjork

[57] ABSTRACT

Pyrrolo[3,4-d]pyrimidines of the following formula:

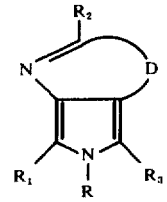

wherein:
R is hydrogen, $(C_{1-4})$alkyl, benzyl or chloro-substituted benzyl;
$R_1$ is hydrogen, $(C_{1-4})$alkyl, phenyl or phenyl substituted with methyl, ethyl, methoxy, hydroxy, chloro, fluoro or bromo;
$R_2$ is hydrogen, $(C_{1-4})$alkyl, phenyl or amino;
$R_3$ is hydrogen or $(C_{1-4})$alkyl;
D is a divalent radical selected from the groups

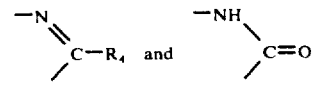

wherein the carbon atoms are linked to the carbon atom of the pyrrole nucleus and $R_4$ represents hydroxy, $(C_{1-4})$alkyl or phenyl; and a salt thereof with a pharmaceutically-acceptable acid. The compounds are useful as antiinflammatories and as prostaglandin synthetase inhibitors.

1 Claim, No Drawings

PYRROLO[3,4-D]PYRIMIDINES AND METHODS FOR THEIR PREPARATION

The present invention relates to new heterocyclic compounds with pharmacological activity of the following general formula

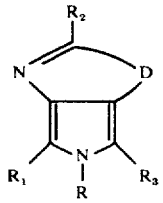

wherein:

R represents hydrogen, $(C_{1-4})$alkyl, e.g. methyl, ethyl, propyl, isopropyl, butyl, isobutyl or tert-butyl, benzyl or chloro substituted benzyl;

$R_1$ stands for hydrogen, $(C_{1-4})$alkyl as above defined, phenyl or phenyl substituted with methyl, ethyl, methoxy, hydroxy, chloro, fluoro or bromo, such as, for instance, p-tolyl, o-tolyl, p-anisyl, m-hydroxyphenyl, p-hydroxyphenyl, o-chlorophenyl, p-fluorophenyl or m-bromophenyl;

$R_2$ may be hydrogen, $(C_{1-4})$alkyl as above defined, phenyl or amino;

$R_3$ is selected from hydrogen or $(C_{1-4})$alkyl as above defined;

D represents a divalent radical selected from the groups

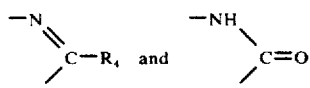

wherein the carbon atoms are linked to the carbon atom of the pyrrole nucleus and $R_4$ represents hydroxy, $(C_{1-4})$alkyl as above defined or phenyl; and to salts therewith of pharmaceutically acceptable acids.

In numbering the substances of the formula I above, the rules of the I.U.P.A.C. have been followed. For the sake of better understanding the basic skeleton ring can be named pyrrolo [3,4-d]pyrimidine and the various positions are numbered as indicated below:

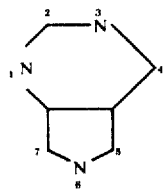

Taking into account the meanings of the group D and the fact that $R_4$ can be hydroxy and $R_2$ amino, it is understandable to any person who is skilled in the art that the compounds of general formula I may exist in different keto-enol and amino-imino tautomeric forms: said forms are in a state of dynamic equilibrium i.e., they rapidly exchange into each other, and are in any case considered as a part of the invention. This characteristic is well known from the chemical literature concerning the amino- and hydroxy-pyrimidines, see for instance R. C. Elderfield, Heterocyclic Compounds, Vol. 6, pages 257-8, John Wiley and Sons Inc., New York, 1957.

The process for preparing the compounds of the invention schematically comprises reacting a β-aminopyrrole derivative of formula

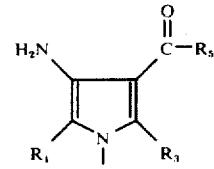

or an acid salt thereof, wherein R, $R_1$ and $R_3$ have the above meanings and $R_5$ is selected from $(C_{1-4})$alkyl as above defined, phenyl or an alkoxy group containing 1 to 4 carbon atoms with a compound of formula $R_6$ — $NH_2$ (III) or an acid salt thereof where $R_6$ represents —CN, —CHO,

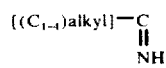

wherein $(C_{1-4})$alkyl is as above defined, or

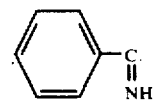

According to a preferred mode of carrying out the process of the invention, a molar proportion of the compound of formula II, or an acid salt thereof is contacted with at least one molar equivalent but, more conveniently, a molar excess of the compound of formula III or an acid salt thereof, preferably in the absence of any solvent even if both reactants are solid substances.

Though not essential, the reaction is advantageously carried out in the presence of catalytic amounts of organic or inorganic acids such as, for instance, hydrohalogenic acids, acetic, sulfuric or p-toluenesulfonic acid. However, owing to the fact that the reaction is preferably carried out in the absence of solvents, it is more convenient to add the necessary amount of the acid combined with a suitable base in form of a salt from which the acid is made free during the course of the reaction. To this purpose salts of tertiary organic nitrogen containing bases with hydrohalogenic acids e.g., piridynium chloride, trimethylammonium chloride, quinolinium bromide and analogs, or even the acid salts of the same reactants of formulas II and III are conveniently employed.

The resulting reaction mixture is then heated at a temperature comprised between about 90° and about 200° C for an interval of time varying from about 1 to about 20 hours.

The compounds of the invention are recovered according to procedures which are entirely familiar to a skilled technician in the form of free bases or as the corresponding salts of pharmaceutically acceptable acids and, if necessary, they are further subjected to common purification techniques, such as, for instance, column chromatography, fractional distillation or recrystallization from suitable solvents.

The foregoing mentioned salts of pharmaceutically acceptable acids are essentially represented by the hydrochloride, hydrobromide, hydroiodide, sulfate, phosphate, benzoate, oxalate, acetate, methanesulfonate, cyclohexylsulfonate and analogs.

These salts possess the same degree of activity of the free bases, and accordingly, they are included within the scopes of the present invention. They are easily obtained by treating a compound of formula I as the free base with the predetermined pharmaceutically acceptable acid. In turn, it is possible to restore the free base from the corresponding salt by reaction with at least one equimolecular amount of a basic agent.

The starting compounds of formula III are commercially available products. The starting substances of formula II are prepared through a process which involves the reaction between an α-aminonitrile of formula:

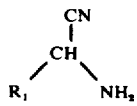

and a β-dicarbonylcompound of formula

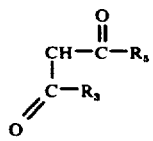

wherein $R_1$, $R_3$ and $R_5$ have the aforesaid meanings. The formed β-aminopyrrole of formula

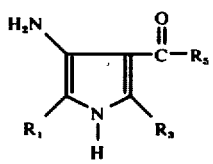

corresponding to the compound of formula II wherein R represents hydrogen, can then be transformed by common chemical procedures into the other desired starting materials of formula II.

The compounds of the invention display very interesting pharmacological properties, more particularly, they are active essentially as antiinflammatories and as prostaglandin synthetase inhibitors.

The antiinflammatory activity was investigated through the "carrageenin induced edema" test in rats, which was performed following substantially the operative scheme proposed by C. A. Winter et al. in Proc. Soc. Expl. Biol. Med., 111, 544, 1962. Representative experiments showed that dose levels ranging from about 100 to about 200 mg/kg. per os of the compounds of Examples 5 and 6 caused decrease of the induced edema in the laboratory animals ranging from about 35 to about 55% over the controls ie., the animals in which edema was induced but which did not receive the substance to be investigated. It must be noted that a percent decrease of the edema of 30 is absolutely significative from the pharmacological standpoint.

These very favorable antiinflammatory properties are coupled with a very low toxicity, being the $LD_{50}$ of the compounds of the invention always higher than 1000 mg/kg. p.o. in mice.

Toxicities were determined substantially according to the method described by Lichtfield and Wilcoxon in Journ. Pharm. Expt. Ther. 96, 99, 1949.

Finally, some of the compounds of the invention display interesting C.N.S. depressant properties and possess a valuable degree of activity on the hydric balance of warm blooded animals.

The compounds of the invention may be administered by various routes.

While the preferred routes of administration are oral and rectal, parenteral administration can also be employed.

For oral administration, the compounds are compounded into pharmaceutical dosage forms, such as, for instance, tablets, capsules, elixirs, solutions and the like. The dosage unit may contain the usual excipients, e.g. starch, gums, fatty acids, alcohols, sugars, etc. For rectal administration the compounds are administered in the form of suppositories, admixed with conventional vehicles, such as, for example, cocoa butter, wax, spermaceti or polyoxyethyleneglycols and their derivatives. The dosage range is from about 0.05 to about 2.00 g. per day, preferably administered in divided dose.

Accordingly the present invention provides a therapeutic composition comprising as the active ingredient a compound of the invention together with a pharmaceutically acceptable carrier.

The following additional description and examples further describe the invention and the manner and process of making and using it to enable the art skilled to make and use the same and set forth the best mode contemplated by the inventors of carrying out the invention.

EXAMPLE 1

2-Amino-4,5-dimethyl-7-phenyl-6H-pyrrolo[3,4-d]pyrimidine hydrochloride 5.0 Grams (0.0234 mole) of 4-acetyl-3-amino-2-methyl-5-phenylpyrrole, 1.0 g. (0.025 mole) of cyanamide and 2.3 g. (0.0198 mole) of pyridinium chloride are intimately mixed by finely grinding in a mortar. The resulting solid mixture is then poured into a flask, cautiously heated to about 100°–130° C and kept at this temperature for fifteen minutes. After cooling, the reaction mass is taken up with 150 ml. of aqueous 10% hydrochloric acid, filtered and the obtained solid is recrystallized from water.

Yield 5.0 g. of the title compound. M.p. 334°–6° C.

EXAMPLE 2

5-Methyl-7-phenyl-6H-pyrrolo[3,4-d]pyrimidine-4(3H)-one

A mixture of 3 g. (0.0107 mole) of 3-amino-4-carbethoxy-5-methyl-2-phenyl-pyrrole hydrochloride and 20 ml. (0.242 mole) of formamide are cautiously heated at 160° C for 16 hours. Upon cooling to room temperature the title compound precipitates as a solid substance, which is recovered by filtration and washed with water.

Yield 2.8 g. M.p. 295°–6° C. The compound needs no further purification.

EXAMPLE 3

5-Methyl-4,7-diphenyl-6H-pyrrolo[3,4-d]pyrimidine

The title compound is obtained following the procedure of the foregoing Example, starting from 3-amino-4-benzoyl-5-methyl-2-phenyl-pyrrole and formamide.
Yield 8%. M.p. 256°–58° C.

EXAMPLE 4

5-Methyl-2,7-diphenyl-6H-pyrrolo[3,4-d]pyrimidine-4(3H)-one 3.8 Grams (0.0136 mole) of 3-amino-4-carbethoxy-5-methyl-2-phenyl-pyrrole hydrochloride and 3.53 g. (0.0228 mole) of benzamidine hydrochloride are intimately mixed by finely grinding in a mortar. The resulting solid mixture is then poured into a flask and cautiously heated to about 140° C and kept at this temperature for 16 hours. After cooling, the reaction mass is taken up with 10 ml. of methanol, filtered and the obtained solid is recrystallized from methanol.

Yield 0.7 g. of the title compound. M.p. 345°–8° C. The following compounds are prepared substantially according to the same procedure of the foregoing Example.

EXAMPLE 5

2,5-Dimethyl-4,7-diphenyl-6H-pyrrolo[3,4-d]pyrimidine, from 3-amino-4-benzoyl-5-methyl-2-phenyl-pyrrole and acetamidine hydrochloride.
Yield 32%. M.p. 308°–10° C (from ethanol/water).

EXAMPLE 6

2,4,5-Trimethyl-7-phenyl-6H-pyrrolo[3,4-d]pyrimidine, from 4-acetyl-3-amino-5-methyl-2-phenyl-pyrrole and acetamidine hydrochloride.
Yield 38%. M.p. 243°–5° C (from methanol/water).

EXAMPLE 7

6-Ethyl-2,5-dimethyl-4,7-diphenyl-6H-pyrrolo[3,4-d]pyrimidine from 3-amino-4-benzoyl-1-ethyl-5-methyl-2-phenyl-pyrrole and acetamidine hydrochloride.
Yield 50%. M.p. 186°–87° C (from methanol/water). Typical compounds which can be prepared pursuant to the procedure outlined in the above examples are:

- 5-Methyl-4-phenyl-7-(p-tolyl)-6H-pyrrolo[3,4-d]pyrimidine
- 4,5-Dimethyl-2-phenyl-7-(p-tolyl)-6H-pyrrolo[3,4-d]pyrimidine
- 5,6-Dibutyl-7-(p-ethylphenyl)-4-propyl-6H-pyrrolo[3,4-d]pyrimidine
- 7-(p-Anisyl)-2-ethyl-4,6-dimethyl-6H-pyrrolo[3,4-d]pyrimidine
- 7-(o-Anisyl)-2-butyl-5-methyl-4-phenyl-6H-pyrrolo[3,4-d]pyrimidine
- 7-(p-Anisyl)-5-methyl-6H-pyrrolo[3,4-d]pyrimidine-4(3H)-one
- 7-(p-Chlorophenyl)-4,5-dimethyl-2-phenyl-6H-pyrrolo[3,4-d]pyrimidine hydrochloride.
- 7-(p-Chlorophenyl)-2,5-dimethyl-4-phenyl-6H-pyrrolo[3,4-d]pyrimidine sulfate.
- 7-(o-Chlorophenyl)-2,5-dimethyl-6H-pyrrolo[3,4-d]pyrimidine-4(3H)-one.
- 7-(p-Hydroxyphenyl)-4,5-dimethyl-6H-pyrrolo[3,4-d]pyrimidine.
- 7-(o-Fluorophenyl)-5-methyl-2,7-diphenyl-6H-pyrrolo[3,4-d]pyrimidine.
- 7-(m-Bromophenyl)-6H-pyrrolo[3,4-d]pyrimidine-4(3H)-one
- 6-Benzyl-2,4,5-trimethyl-7-phenyl-6H-pyrrolo[3,4-d]pyrimidine hydroiodide.
- 6-(p-Chlorobenzyl)-4-methyl-2,7-diphenyl-6H-pyrrolo[3,4-d]pyrimidine.
- 5,6,7-Trimethyl-4-phenyl-6H-pyrrolo[3,4-d]pyrimidine
- 5,7-Dimethyl-4-phenyl-6H-pyrrolo[3,4-d]pyrimidine
- 5,6-Dibutyl-7-ethyl-4-propyl-6H-pyrrolo[3,4-d]pyrimidine.
- 5,7-Dimethyl-6H-pyrrolo[3,4-d]pyrimidine-4(3H)-one.

PREPARATION OF THE STARTING β-AMINOPYRROLES OF FORMULA II

A. 4-Acetyl-3-amino-5-methyl-2-phenyl-pyrrole a. A solution of 2 g. (0.015 mole) of 2-amino-2-phenylacetonitrile and 1.4 g. (0.014 mole) of acetylacetone in 30 ml. of anhydrous benzene is refluxed for 2 hours on an oil bath in the presence of 100 mg. of p-toluenesulfonic acid. After cooling, the reaction mixture is filtered, then the solvent is evaporated off to give an oily residue which is distilled under reduced pressure; the fraction boiling at 150° C/0.1 mmHg. is collected.

b. 0.40 Grams of sodium are dissolved in 15 ml. of anhydrous ethanol, then a solution of 2.5 g. of the fraction boiling at 150° C/0.1 mmHg. prepared as in point (a) in anhydrous ethanol is added dropwise and the mixture is allowed to stand at room temperature for 4 hours. After bubbling dry hydrogen chloride in the ethanol solution, a precipitate forms, which is recovered by filtration and recrystallized from ethanol/diethyl ether. Yield 2.0 g. of the title compound as the corresponding hydrochloride, which melts at 242° C (with decomposition). The title compound is obtained by extraction with ethyl acetate of an aqueous solution of the hydrochloride alkalinized with 5% sodium hydroxide. M.p. 220° C (from methanol).

According to the procedure described in the previous Example the following starting compounds of formula II have been prepared.

| COMPOUND | M.p.° C |
|---|---|
| B) 3-Amino-4-benzoyl-5-methyl-2-phenyl-pyrrole | 203–5 |
| C) 3-Amino-4-carbethoxy-5-methyl-2-phenyl-pyrrole hydrochloride | 249–52 |

PREPARATION OF

D. 3-Amino-4-benzoyl-1-ethyl-5-methyl-2-phenyl-pyrrole

The synthesis of this compound starts from compound (B) which is reacted with benzaldehyde to the corresponding Schiff's base. This product is subsequently treated in strong alkaline solution with ethyliodide, whereby 3-benzylideneamino-4-benzoyl-1-ethyl-5-methyl-2-phenyl-pyrrole (m.p. 147°–48° C) is obtained. This compound is then hydrolized under mild acidic conditions to the title substance (M.p. 238°–40° C).

We claim:
1. Compound of formula

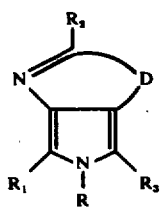

wherein:
R represents hydrogen, (C$_{1-4}$)alkyl, benzyl or chloro substituted benzyl;
R$_1$ stands for hydrogen, (C$_{1-4}$)alkyl, phenyl, or phenyl substituted with methyl, ethyl, methoxy, hydroxy, chloro, fluoro or bromo;
R$_2$ may be hydrogen, (C$_{1-4}$)alkyl, phenyl or amino;
R$_3$ is selected from hydrogen or (C$_{1-4}$)alkyl;
D represents a divalent radical selected from the groups

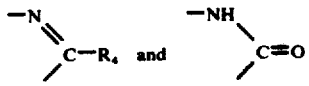

wherein the carbon atoms are linked to the carbon atom of the pyrrole nucleus and R$_4$ represents hydroxy, (C$_{1-4}$)alkyl or phenyl;
and a salt thereof with a pharmaceutically acceptable acid.

* * * * *